(12) United States Patent
Im

(10) Patent No.: US 10,288,587 B2
(45) Date of Patent: May 14, 2019

(54) METHOD FOR MONITORING SIGNAL HAVING MULTI-BAND FREQUENCY

(71) Applicant: Globiz Co., Ltd., Seoul (KR)

(72) Inventor: Jong Soon Im, Seoul (KR)

(73) Assignee: Globiz Co., Ltd., Seoul (KR)

( * ) Notice: Subject to any disclaimer, the term of this patent is extended or adjusted under 35 U.S.C. 154(b) by 263 days.

(21) Appl. No.: 15/314,080

(22) PCT Filed: May 21, 2015

(86) PCT No.: PCT/KR2015/005104
§ 371 (c)(1),
(2) Date: Nov. 27, 2016

(87) PCT Pub. No.: WO2015/182921
PCT Pub. Date: Dec. 3, 2015

(65) Prior Publication Data
US 2017/0199163 A1   Jul. 13, 2017

(30) Foreign Application Priority Data

May 27, 2014   (KR) .................. 10-2014-0063880

(51) Int. Cl.
| | |
|---|---|
| G01N 29/46 | (2006.01) |
| G01N 29/12 | (2006.01) |
| G01N 29/42 | (2006.01) |
| G01R 23/02 | (2006.01) |
| G01N 29/14 | (2006.01) |

(52) U.S. Cl.
CPC ............ *G01N 29/46* (2013.01); *G01N 29/12* (2013.01); *G01N 29/14* (2013.01); *G01N 29/42* (2013.01); *G01R 23/02* (2013.01); *G01N 2291/0258* (2013.01)

(58) Field of Classification Search
CPC ........ G01N 29/46; G01N 29/14; G01N 29/12; G01N 29/42; G01N 2291/0258; G01R 23/02
See application file for complete search history.

(56) References Cited

U.S. PATENT DOCUMENTS

2017/0199163 A1 * 7/2017 Im .................. G01R 23/02

FOREIGN PATENT DOCUMENTS

| JP | 02-573254 | 1/1997 | |
|---|---|---|---|
| JP | 11-148858 | 6/1999 | |
| JP | 11-194048 | 7/1999 | |
| JP | 2006-292601 | 10/2006 | |
| WO | WO 2015/182921 | 12/2015 | |
| WO | WO-2015182921 A1 * | 12/2015 | ............ G01R 23/02 |

OTHER PUBLICATIONS

International Search Report and the Written Opinion dated Jun. 22, 2015 From the Korean Intellectual Property Office Re. Application No. PCT/KR2015/005104. (9 Pages).

* cited by examiner

*Primary Examiner* — Daniel Pihulic

(57) ABSTRACT

The present invention relates to a method for monitoring a signal having a multi-band frequency. The method for monitoring a signal having a multi-band frequency detected in a target to be monitored includes: dividing the multi-band frequency into at least two regions; setting update periods to be different from each other for each of the divided frequency bands; and displaying monitoring states of the divided frequency bands depending on the update periods set to be different from each other.

5 Claims, 6 Drawing Sheets

METHOD FOR MONITORING SIGNAL HAVING MULTI-BAND FREQUENCY

RELATED APPLICATIONS

This application is a National Phase of PCT Patent Application No. PCT/KR2015/005104 having International filing date of May 21, 2015, which claims the benefit of priority of Korean Patent Application No. 10-2014-0063880 filed on May 27, 2014. The contents of the above applications are all incorporated by reference as if fully set forth herein in their entirety.

FIELD AND BACKGROUND OF THE INVENTION

The present invention relates to a method for monitoring a signal having a multi-band frequency, and more particularly, to a method for monitoring a signal having a multi-band frequency capable of effectively and precisely monitoring signals having various frequency bands from a low frequency band generated in a facility such as building up to a high frequency band.

Generally, a state monitoring system of a machine system or a health monitoring system of a building has used several signal interpreting methods in order to diagnose the machine system and the building.

For example, a fast-Fourier transform (FFT) interpreting method or an application interpreting method based on the FFT analyzing method has been universally used in the state monitoring system of the machine system or the health monitoring system of the building.

In order to use the FFT interpreting method, it is an important factor to determine an entire frequency band of interest and a frequency resolution.

Since a maximum ratio between revolutions per minute (RPMs) of input and output terminals of a gear transmission and an accelerator/decelerator included in the machine system may be 100 or more, it is inevitable to select a wide frequency band.

Meanwhile, since behavior of a low speed region is very important, a high resolution of a low speed frequency band is simultaneously required. For example, in the case of the building, a natural frequency is mainly within 1 Hz and disturbance of wind and earthquake becomes about up to 100 Hz, and thus, interpretation in a wide frequency band is required in the building.

In order to perform a wide band high resolution frequency analysis, data sampled at a high speed over a long period of time should be acquired, and integrated FFT should be performed on the acquired data.

That is, since an entire interpretation frequency band corresponds a half of a sampling rate, when the entire frequency band is large, the sampling rate cannot but be large. In addition, since the high resolution corresponds to an inverse number of an entire measurement time, measurement for a long period of time is required in order to obtain the high resolution, and a capacity of a storage for storing related data therein cannot but become large.

Therefore, an amount of data sampled for a long period of time is vast, such that a huge amount of calculation is required in the case in which the FFT is performed on the vast amount of data at the same time, which is very disadvantageous in terms of real-time monitoring.

For example, in an actual structural health monitoring system (SHM), the FFT may be performed on numerous data (about 260,000 data) measured at a sampling rate of about 200 Hz for about 20 minutes.

Therefore, in the case in which an amount of data frequency-sampled for a long period of time is vast, an amount of calculation is very large and a size of one set of data is vast, such that it is difficult to manage a database, and a time interval between records for managing the data is very large, such that it is difficult to analyze a tendency.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method for monitoring a signal having a multi-band frequency having advantages of effectively and economically analyzing the multi-band frequency by performing immediate fast-Fourier transform (FFT) on a high frequency band in which a real time change is reflected to represent a performing result, representing a change at an intermediate-level frequency in an intermediate frequency band, and representing a change at a low frequency in a low frequency band.

An exemplary embodiment of the present invention provides a method for monitoring a signal having a multi-band frequency detected in a target to be monitored, including: dividing the multi-band frequency into at least two regions; setting update periods to be different from each other for each of the divided frequency bands; and displaying monitoring states of the divided frequency bands depending on the update periods set to be different from each other.

In the setting of the update periods to be different from each other for each of the divided frequency bands, an update period corresponding to a high frequency band may be set to be shorter than an update period corresponding to a lower frequency band.

A sampling rate for obtaining monitoring signals for each of the divided frequency bands may be set to be larger in a high frequency band than in a low frequency band.

The target to be monitored may be a building in which a multi-band frequency 0.1 to 100 Hz is detected.

After an entire multi-band frequency of the target to be monitored is initially displayed, monitoring signals having the respective divided frequency bands may be independently displayed depending on the set update periods.

As described above, according to an exemplary embodiment of the present invention, it is possible to effectively and economically analyze a multi-band frequency by performing immediate fast-Fourier transform (FFT) on a high frequency band in which a real time change is reflected and monitored to represent a performing result, representing a change at an intermediate-level frequency in an intermediate frequency band, and representing a change at a low frequency in a low frequency band.

DESCRIPTION OF SPECIFIC EMBODIMENTS OF THE INVENTION

Hereinafter, exemplary embodiments of the present invention will be described more fully with reference to the accompanying drawings so as to be easily practiced by those skilled in the art to which the present invention pertains. However, the present invention is not limited to exemplary embodiments described therein, but may also be embodied in other forms.

Throughout the present specification, unless explicitly described to the contrary, "comprising" any components will be understood to imply the inclusion of other components rather than the exclusion of other components.

Figure 1:
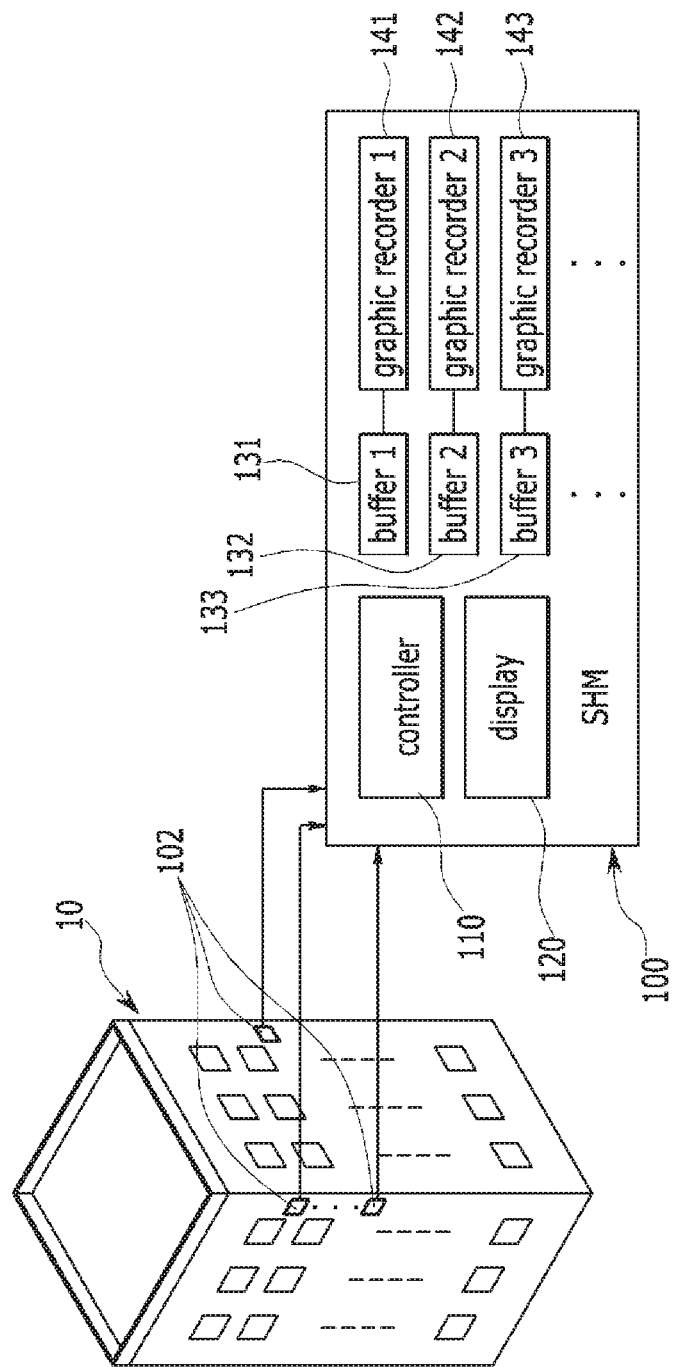
FIG. 1 is a drawing showing a building as an example of a target to be monitored to which a method for monitoring a signal having a multi-band frequency according to an exemplary embodiment of the present invention may be applied.

FIG. 1 is a drawing showing a building as an example of a target to be monitored to which a method for monitoring a signal having a multi-band frequency according to an exemplary embodiment of the present invention may be applied and a structural health monitoring system (SHM) for monitoring this building.

Referring to FIG. 1, a plurality of sensors 102 for detecting and monitoring vibrations, or the like, generated in a building 10 are installed at determined positions of the building 10. Installation positions of the sensors 102 may be determined on walls, pillars, and the like, of the building 10 through consultation with an architect.

The sensors 102 may be sensors that may detect the vibrations, or the like, of the building 10 generated due to wind, earthquake, internal/external disturbance, or the like. Since a frequency that may be generated in the building 10 may have a wide range from a low frequency band to a high frequency band (for example, about 0.1 Hz to 100 Hz), the sensors 120 may be sensors that may detect an entire frequency in this range without loss.

Signals detected by the sensors 102 are transferred to and analyzed in a structural health monitoring system (SHM) 100.

The structural health monitoring system (SHM) 100 may include a controller 110 for controlling a general operation of the SHM, a display 120 for displaying a monitoring content and result processed in the SHM, buffers 131, 132, and 133 for recording and storing signals for each of frequency bands (for example, a low frequency, an intermediate frequency, a high frequency) therein, and graphic recorders 141, 142, and 143 for representing data recorded and stored in the buffers 131, 132, and 133 by a graph under a control of the controller 110.

An interpreter, an analyzer, and a processor interpreting, analyzing, and processing monitoring signals may be included in the controller 110.

Existing buffers and graphic recorders may be used as the buffer 131, 132, and 133 and the graphic recorders 141, 142, and 143, respectively.

The SHM 100 according to an exemplary embodiment of the present invention may include a database for storing signals and data therein, a noise filter for removing noise included in the signals, and the like, as in a general SHM, although not shown.

Figure 2:
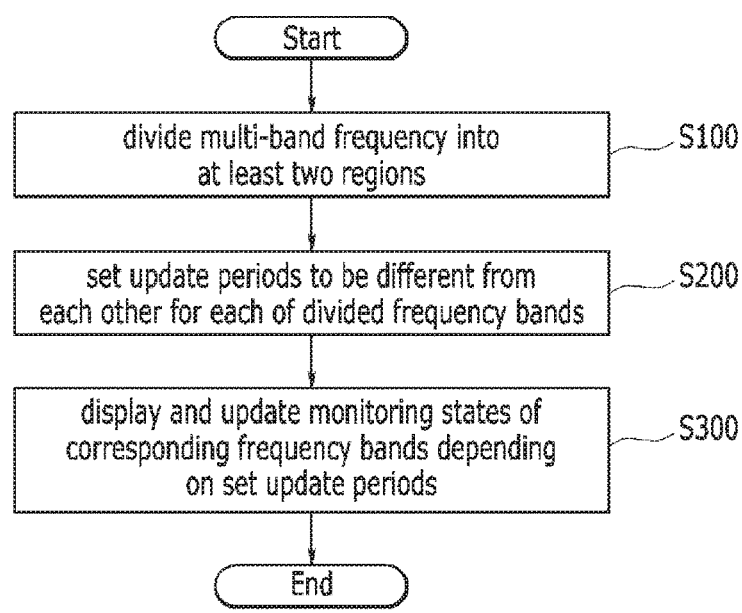
FIG. 2 is a flow chart of a method for monitoring a signal having a multi-band frequency according to an exemplary embodiment of the present invention.

FIG. 2 is a flow chart of a method for monitoring a signal having a multi-band frequency according to an exemplary embodiment of the present invention.

Figure 3:
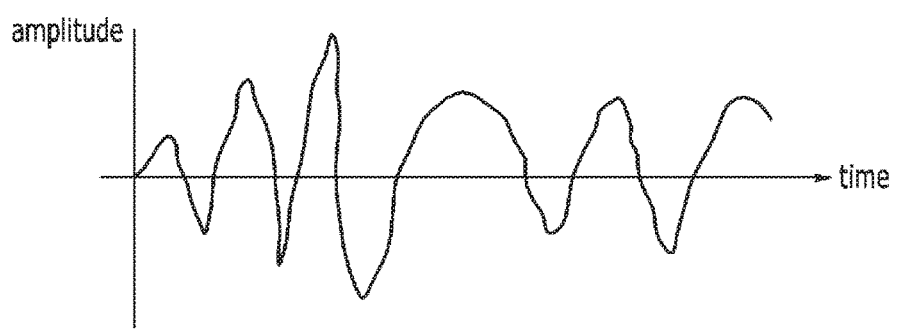
FIG. 3 is an illustrative diagram of a monitoring signal of a building according to an exemplary embodiment of the present invention.

Referring to FIG. 2, the SHM 100 may divide a multi-band frequency included in a monitoring signal of the building as shown in FIG. 3 into at least two regions (bands) (S100).

For example, the SHM 100 may divide the multi-band frequency into three frequency bands such as a low frequency band (for example, 0 to 1 Hz), an intermediate frequency band (for example, 1 to 10 Hz), and a high frequency band (for example, 10 to 100 Hz).

Different resolutions may be applied to the respective divided frequency bands. For example, a 10-3 resolution may be applied to the low frequency band, a 10-2 resolution may be applied to the intermediate frequency band, and a 10-1 resolution may be applied to the high frequency band. The application of the resolutions described above follows a signal processing technology.

The SHM 100 may obtain the signals detected by the sensors 102 by applying different sampling rates to each of the divided frequency bands. For example, the SHM 100 may obtain a monitoring signal at a sampling rate of about 200 Hz in the high frequency band, obtain a monitoring signal at a sampling rate of about 20 Hz in the intermediate frequency band, and obtain a monitoring signal at a sampling rate of about 2 Hz in the low frequency band.

It will be obvious to a person of an ordinary skill in the art that the reason why the sampling rate becomes large from the low frequency band to the high frequency band as described above is that a signal is frequently changed in a short time in the high frequency band. In addition, in an exemplary embodiment of the present invention, different numbers of samplings may be applied to each of the frequency bands, and the number of samplings may be set to be larger in the low frequency band than in the high frequency band.

Signals obtained in each of the frequency bands to which the different sampling rates or the different numbers of samplings are applied as described above may be stored in the corresponding buffers 131, 132, and 133. Since the buffer 131 storing the signal having the high frequency band therein should record and store a larger amount of signals therein than that of the buffer 133 storing the signal having the low frequency band therein or more frequently update data as compared with the buffer 133 storing the signal having the low frequency band therein, the buffer 131 may have a relatively large capacity or relatively good reliability.

Figure 4:
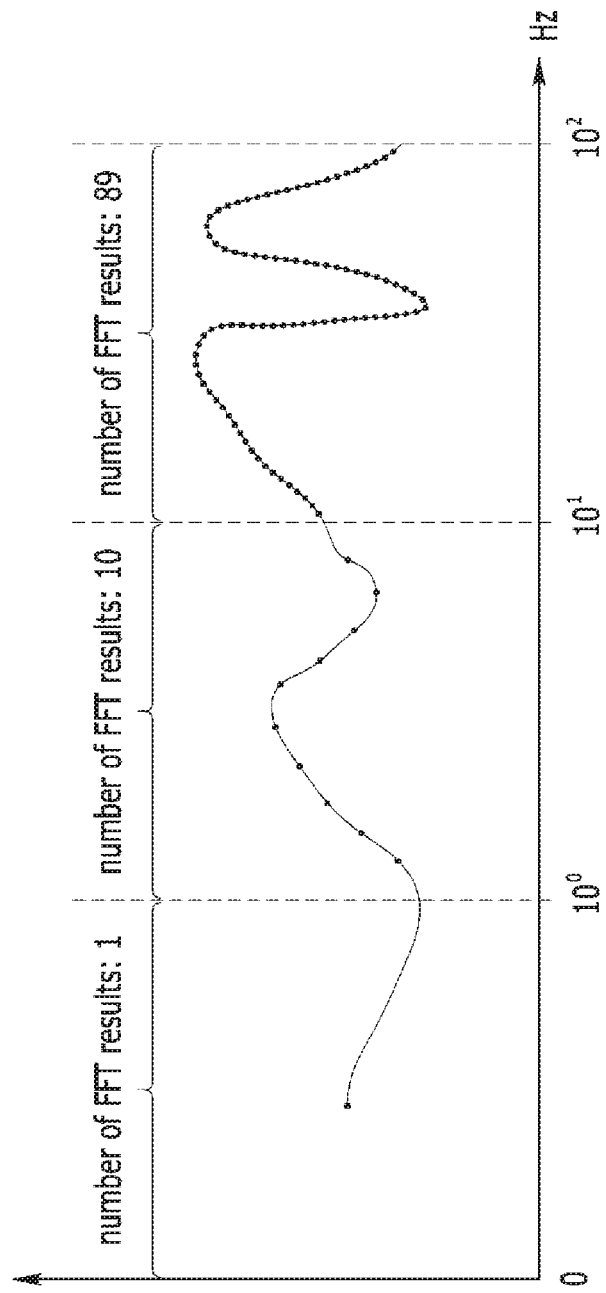
FIGS. 4, 5 and 6 are drawings for describing the method for monitoring a signal having a multi-band frequency according to an exemplary embodiment of the present invention.

For example, about 200, 20, and 2 data collected for 1 second are filled in the respective buffers 131, 132, and 133, respectively, 100 fast Fourier transform (FFT) results are calculated when FFT is performed on the data filled in the respective buffers, and a signal obtained on the basis of the 100 FFT results may be displayed in a form as shown in FIG. 4.

As described above, since a difference is present among amounts of data collected in the respective buffers for, for example, 1 second, that is, since a large amount of data are collected even for a short time in the buffer 131 corresponding to the high frequency band, the data need to be updated per short time period, but since a sufficient amount of data are not collected for a short time (for example, 1 second) in the buffers 132 and 133 each corresponding to the intermediate frequency band and/or the low frequency band, the signal data having the corresponding frequency bands do not need to be updated per short time period as in the signal data having the high frequency band.

For example, a display update period of the signal data corresponding to the high frequency band may be about 1 second, a display update period of the signal data corresponding to the intermediate frequency band may be about 10 seconds, and a display update period of the signal data corresponding to the low frequency band may be about 100 seconds (S200).

In this case, a change trend of the signal corresponding to the high frequency band may be immediately analyzed, and change trends of the signals corresponding to the intermediate frequency band and/or the low frequency band may be analyzed at appropriate time intervals, such that the signals may be efficiently monitored, thereby making it possible to efficiently process the data.

Figure 5:
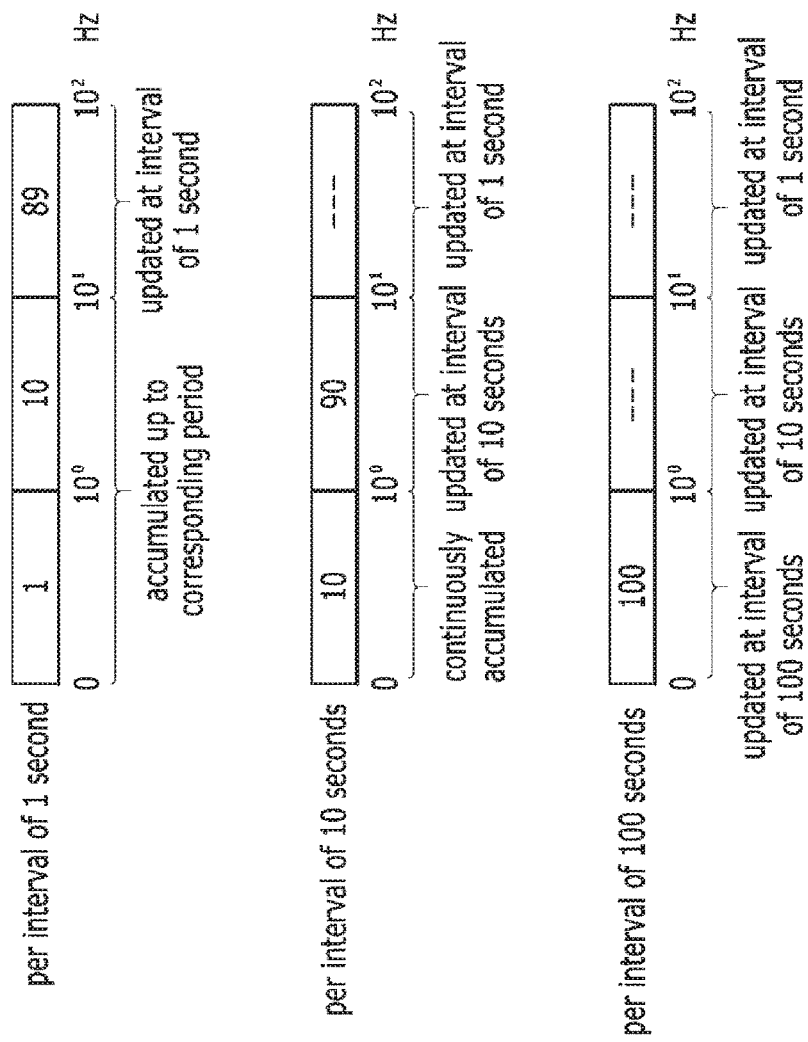

The numbers of FFT results recorded in the respective buffers 131, 132, and 133 per time are shown by way of example in FIG. 5. A monitoring graph in which the signal data having the corresponding frequency bands are updated on the basis of the numbers of FFT results shown in FIG. 5 is shown in FIG. 6.

That is, the SHM 100 according to an exemplary embodiment of the present invention may display signal monitoring states of the corresponding frequency bands depending on update periods set to be different from each other for each of the corresponding frequency bands (S300).

Figure 6:
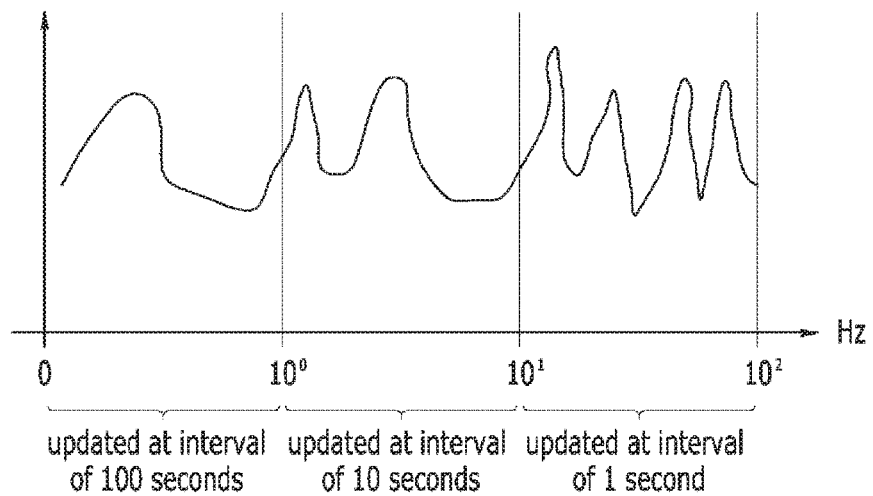

Referring to FIG. 6, forms of a graph corresponding to the respective frequency bands may be independently updated or be precisely represented depending on update periods set for each of the frequency bands under a control of the controller 110 of the SHM 100.

Since FFT result processing of the respective buffers 131, 132, and 133 of FIG. 5 and a data mapping method for updating the graph for each of the frequency bands of FIG. 6 may be easily performed by a person of an ordinary skilled in the art using an existing technology, a description therefor will be omitted for simplification of explanation.

In addition, the SHM 100 according to an exemplary embodiment of the present invention may initially display an entire multi-band frequency of the target to be monitored, and then update and display monitoring signals having the respective divided frequency bands in the same chart or update and display the monitoring signals at independent frequencies for each of the frequency regions in independent charts, depending on the update periods set to be different from each other for each of the frequency bands.

According to the forms of the graph shown in FIG. 6, a current state of the signal having the high frequency band generated in the building may be immediately analyzed in substantially real time, and since the signals having the intermediate frequency band and the high frequency band are more precisely displayed as an update period becomes short, current states of the signals having the intermediate frequency band and the high frequency band may be precisely analyzed with the passage of time.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A method for monitoring a signal having a multi-band frequency detected in a target to be monitored, comprising:
   dividing the multi-band frequency into at least two regions;
   setting update periods to be different from each other for each of the divided frequency bands; and
   displaying monitoring states of the divided frequency bands depending on the update periods set to be different from each other;
   wherein in the setting of the update periods to be different from each other for each of the divided frequency bands, an update period corresponding to a high frequency band is set to be shorter than an update period corresponding to a lower frequency band.

2. A method for monitoring a signal having a multi-band frequency detected in a target to be monitored, comprising:
   dividing the multi-band frequency into at least two regions;
   setting update periods to be different from each other for each of the divided frequency bands; and
   displaying monitoring states of the divided frequency bands depending on the update periods set to be different from each other;
   wherein a sampling rate for obtaining monitoring signals for each of the divided frequency bands is set to be larger in a high frequency band than in a low frequency band, and the number of samplings is set to be larger in the low frequency band than in the high frequency band.

3. The method for monitoring a signal having a multi-band frequency of claim 1, wherein:
   the target to be monitored is a building in which a multi-band frequency 0.1 to 100 Hz is detected.

4. The method for monitoring a signal having a multi-band frequency of claim 1, wherein:
   after an entire multi-band frequency of the target to be monitored is initially displayed, monitoring signals having the respective divided frequency bands are independently displayed depending on the set update periods.

5. A method for monitoring a signal having a multi-band frequency detected in a target to be monitored, comprising:
   dividing the multi-band frequency into at least two regions;
   setting update periods to be different from each other for each of the divided frequency bands; and
   displaying monitoring states of the divided frequency bands depending on the update periods set to be different from each other;
   wherein different resolutions are applied to the respective divided frequency bands, respectively.

* * * * *